United States Patent
McSweeney et al.

(10) Patent No.: US 11,793,768 B2
(45) Date of Patent: *Oct. 24, 2023

(54) METHODS FOR THE NON-THERAPEUTIC ALLEVIATION OR PROPHYLAXIS OF SYMPTOMS OF OXIDATIVE STRESS, REDUCED IMMUNE SYSTEM OR CARTILAGE DAMAGE OF RUMINANTS

(71) Applicant: DSM IP ASSETS B.V., Heerlen (NL)

(72) Inventors: Chris McSweeney, St. Lucia (AU); Gonzalo Martinez Fernandez, St. Lucia (AU); Stuart Edward Denman, St. Lucia (AU); Horst Joachim Paul Peter Schirra, Brisbane (AU)

(73) Assignee: DSM IP ASSETS B.V., Heerlen (NL)

(*) Notice: Subject to any disclaimer, the term of this patent is extended or adjusted under 35 U.S.C. 154(b) by 117 days.

This patent is subject to a terminal disclaimer.

(21) Appl. No.: 16/960,373

(22) PCT Filed: Jan. 23, 2019

(86) PCT No.: PCT/EP2019/051596
§ 371 (c)(1),
(2) Date: Jul. 7, 2020

(87) PCT Pub. No.: WO2019/145346
PCT Pub. Date: Aug. 1, 2019

(65) Prior Publication Data
US 2020/0352876 A1    Nov. 12, 2020

(30) Foreign Application Priority Data

Jan. 24, 2018 (EP) .................................... 18153282

(51) Int. Cl.
| | |
|---|---|
| *A61K 31/047* | (2006.01) |
| *A23K 50/10* | (2016.01) |
| *A23K 20/10* | (2016.01) |
| *A61K 31/02* | (2006.01) |
| *A61K 31/04* | (2006.01) |
| *A61K 47/02* | (2006.01) |
| *A61K 9/14* | (2006.01) |

(52) U.S. Cl.
CPC ............ *A61K 31/047* (2013.01); *A23K 20/10* (2016.05); *A23K 50/10* (2016.05); *A61K 31/02* (2013.01); *A61K 31/04* (2013.01); *A61K 47/02* (2013.01); *A61K 9/14* (2013.01)

(58) Field of Classification Search
CPC ...... A61K 31/047; A61K 31/02; A61K 31/04; A61K 47/02; A61K 9/14; A23K 20/10; A23K 50/10
See application file for complete search history.

(56) References Cited

U.S. PATENT DOCUMENTS

2009/0022826 A1    1/2009    Shrier et al.

FOREIGN PATENT DOCUMENTS

| CN | 106540129 | 3/2017 |
|---|---|---|
| EP | 1 560 804 | 8/2005 |
| WO | 01/26482 | 4/2001 |
| WO | 2009/150264 | 12/2009 |
| WO | 2012/084629 | 6/2012 |

OTHER PUBLICATIONS

Matthew Butawan, et al., "Methylsulfonylmethane: Applications and Safety of a Novel Dietary Supplement", Nutrients, vol. 9, No. 3, Mar. 16, 2017, 21 pages.
Evert C. Duin, et al., "Mode of action uncovered for the specific reduction of methane emissions from ruminants by small molecule 3-nitrooxypropanol", Proceedings of the National Academy of Sciences of the United States of America, May 2, 2016, 6 pages.
G.W. Lanigan, "Metabolism of Pyrroltztdine Alkaloids in the Ovine Rumen. IV.* Effects of Chloral Hydrate and Halogenated Methanes on Rumen Methanogenesis and Alkaloid Metabolism in Fistulated Sheep", Australian Journal of Agricultural Research, vol. 23, No. 6, Jan. 1, 1972, 7 pages.
Gonzalo Martinez-Fernandez, et al., "3-NOP vs. Halogenated Compound: Methane Production, Ruminal Fermentation and Microbial Community Response in Forage Fed Cattle", Frontiers in Microbiology, vol. 9, Jan. 1, 2018, 14 pages.
International Search Report for PCT/EP2019/051596 dated Apr. 26, 2019, 5 pages.
Written Opinion of the ISA for PCT/EP2019/051596 dated Apr. 26, 2019, 7 pages.

*Primary Examiner* — Snigdha Maewall
(74) *Attorney, Agent, or Firm* — NIXON & VANDERHYE P.C.

(57) ABSTRACT

The present invention relates to the reduction of oxidative stress, the improvement of the system, the provision of healthy cartilage, as well as the alleviation of pain in ruminants.

14 Claims, No Drawings

METHODS FOR THE NON-THERAPEUTIC ALLEVIATION OR PROPHYLAXIS OF SYMPTOMS OF OXIDATIVE STRESS, REDUCED IMMUNE SYSTEM OR CARTILAGE DAMAGE OF RUMINANTS

This application is the U.S. national phase of International Application No. PCT/EP2019/051596 filed Jan. 23, 2019 which designated the U.S. and claims priority to EP Patent Application No. 18153282.1 filed Jan. 24, 2018, the entire contents of each of which are hereby incorporated by reference.

The present invention relates to the reduction of oxidative stress, the improvement of the immune system, the provision of healthy cartilage, as well as the alleviation of pain in ruminants.

Methylsulfonylmethane (MSM, also known as dimethylsulfone), is a naturally occurring organosulfur compound and a putative methyl donor which is known to have several health benefits such as reducing oxidative stress, lessening of inflammation, reducing muscle spasm, improving the immune system, providing healthy cartilage as well as the alleviating pain e.g. accompanying inflammatory diseases such as arthritis in animals and humans as e.g. outlined in Nutrients. 2017 March; 9(3): 290.

Methylsulfonylmethane naturally occurs in body fluids and tissues as well as in a variety of fresh foods including most fruits and vegetables, milk, and grains. Furthermore, it is marketed as a dietary supplement for humans and animals. Although present in a variety of foods, methylsulfonylmethane is readily lost due to its volatile nature. In addition, methylsulfonylmethane is not yet everywhere approved as feed additive for ruminants. Thus, there is an ongoing need for ingredients which stimulate the endogenous production of methylsulfonylmethane in ruminants in order to profit from its extraordinary health benefits.

Trimethylamine is a known flavoring substances and as such authorized for use in food and feed applications Trimethylamine, however, is also a known methyl donor, which is typically found in enzymatic reactions using the cofactor vitamin B12, which contributes to methyl transfer pathways including e.g. methionine biosynthesis.

Methylation is a critical epigenetic modification influencing metabolism, immune function, and overall health of animals. The lack of methyl donors can thus negatively influence tissue metabolism and immune function at least in part by altering gene expression. Thus, it is nowadays almost routine to supplement animal feed with methyl donors to help maintain the 1-carbon pool in both monogastrics and ruminants.

Common dietary methyl donors used in animal feed are choline and methionine. In ruminants, however, dietary choline and methionine is rapidly and extensively degraded in the rumen, which consequently results in a significant loss of the respective methyl donor. Thus, there is also an ongoing need for ingredients which stimulate the endogenous production of (putative) methyl donors such as MSM or triethylamine in ruminants to profit from the positive health benefits thereof.

Surprisingly it has now been found, that the supplementation of propanediol mononitrate respectively chloroform to ruminants leads to a significant increase of methylsulfonylmethane and triethylamine in the rumen fluid.

Thus, the present invention relates to propandiol mononitrate or chloroform or compositions comprising propandiol mononitrate or chloroform for use in reducing oxidative stress, lessening of inflammation, reducing muscle spasm, improving the immune system, providing healthy cartilage as well as alleviating pain e.g. accompanying inflammatory diseases such as arthritis in ruminants.

In another embodiment, the invention relates to the use of propandiol mononitrate or chloroform for increasing endogeneous methyl donors such as in particular methylsulfonylmethane and triethylamine in the rumen fluid of a ruminant.

In a further embodiment, the present invention relates to a method of increasing endogeneous methyl donors such as in particular methylsulfonylmethane and triethylamine in the rumen fluid of a ruminant, said method encompassing the step of administering propandiol mononitrate or chloroform or compositions comprising propandiol mononitrate or chloroform to a ruminant in need thereof for an effective period of time.

Another object is to provide a method for improving overall health and resistance to disease of a ruminant, said method encompassing administering an effective amount of propandiol mononitrate or chloroform or compositions comprising propandiol mononitrate or chloroform to the ruminant in need thereof.

In a further aspect, this invention relates to a method of increasing the amount of metabolizable sulfur in a ruminant which method comprises providing to the animal in need thereof for ingestion an effective amount of propandiol mononitrate or chloroform or compositions comprising propandiol mononitrate or chloroform.

In another aspect, the present invention relates to a method for the non-therapeutic alleviation of or prophylaxis against oxidative stress, said method including administering propandiol mononitrate or chloroform or compositions comprising propandiol mononitrate or chloroform to a ruminant prior to experiencing oxidative stress, while experiencing oxidative stress and/or after having experienced oxidative stress said method encompassing the consecutive steps of a.) assessing a present or future oxidative stress situation for a ruminant (in order to determine a ruminant in need of treatment) and b.) administering to the ruminant in need thereof an effective amount of the propandiol mononitrate or chloroform or compositions comprising propandiol mononitrate or chloroform.

In yet another aspect, the present invention relates to a method for the non-therapeutic improvement of the immune system, said method including administering propandiol mononitrate or chloroform or compositions comprising propandiol mononitrate or chloroform to a ruminant in need of an improvement of the immune system, said method encompassing the consecutive steps of a.) assessing the immune system of a ruminant in order to determine a ruminant in need of treatment and b.) administering to the ruminant in need thereof an effective amount of the propandiol mononitrate or chloroform or compositions comprising propandiol mononitrate or chloroform.

In a further aspect, the present invention relates to a method for the non-therapeutic provision of healthy cartilage, said method including administering propandiol mononitrate or chloroform or compositions comprising propandiol mononitrate or chloroform to a ruminant prior to experiencing cartilage problems, while experiencing cartilage problems and/or after having experienced cartilage problems, said method encompassing the consecutive steps of a.) determining a cartilage damage in a ruminant e.g. by determining an injury or trauma, determining a joint stiffness and/or swelling and/or determining a clicking or grinding sensation in the joint (in order to determine a ruminant in need of treatment) and b.) administering to the ruminant in need thereof an effective amount of the propandiol mononitrate or chloroform or compositions comprising propandiol mononitrate or chloroform.

Most preferred in all embodiments of the present invention is the use of propanediol mononitrate, which is particularly effective.

In the present context, a ruminant is a mammal of the order Artiodactyla that digests plant-based food by initially softening it within the animal's first stomach, known as the rumen, then regurgitating the semi-digested mass, now known as cud, and chewing it again. The process of again chewing the cud to further break down plant matter and stimulate digestion is called "ruminating".

Ruminants according to the present invention include cattle, goats, sheep, giraffes, American bison, European bison, yaks, water buffalo, deer, camels, alpacas, llamas, wildebeest, antelope, pronghorn, and nilgai.

Propanediol mononitrate (also referred to 1,3-propanediol mononitrate or PDMN [CAS-No: 100502-66-7]) is a known compound which can e.g. be manufactured as outlined in WO2004043898 or WO2012084629 and is available at DSM Nutritional Products Ltd.

The composition according to the present invention are preferably administered to the ruminant for an effective period of time to reduce oxidative stress, to improve the immune system, to provide healthy cartilage and/or to alleviate pain accompanying inflammatory diseases.

In any or all of the above embodiments, propanediol mononitrate or chloroform respectively the composition comprising propanediol mononitrate or chloroform is administered to the animal for an effective period of time to improve the immune system, to provide healthy cartilage and/or to alleviate pain accompanying inflammatory diseases, in particular at set intervals. The set interval can be daily, or it can be more or less frequently than that. Preferably, the set interval is daily.

The effective period of time may be easily selected by a person skilled in the art based on the symptoms and the severity of the symptoms and may be at least 1 day, at least 3 days, at least 7 days, at least 20 days, at least 30 days, at least 60 days, or at least 90 days or periods of time lasting from 1 day to 200 days, from 1 day to 90 days, from 1 day to 60 days, from 1 day to 45 days, from 1 day to 30 days or from 3 days to 21 days.

In all embodiments of the present invention the effective period of time is preferably the time during the experience of symptoms of pain, oxidative stress, a reduced immune system (e.g. during experiencing a disease) and/or cartilage problem, which period can be easily determined by a person skilled in the art. Exemplary periods are periods of about 0.05 hours to about 12 weeks, preferably of about 1 hours to about 8 weeks, most preferably of about 1 day to 4 weeks.

If the treatment is prophylactically, then in all embodiments of the present invention the effective period of time is preferably within a period of 1 day to 4 weeks, preferably of about 1 week to about 3 weeks, most preferably of about 1 week to about 2 weeks prior to the envisaged experience of the symptoms of pain, oxidative stress, a reduced immune system (e.g. during experiencing a disease) and/or cartilage problems.

The term 'an effective amount' as used herein refers to an amount necessary to obtain a physiological effect. The physiological effect may be achieved by one single dose or by repeated doses. The effective amount of propanediol mononitrate or chloroform in the methods according to the invention may vary depending upon known factors, such as the physiological characteristics of the particular composition and its mode and route of administration; the age, health and weight of the ruminant; the nature and extent of the symptoms; the kind of concurrent treatment; the frequency of treatment; and the effect desired which can be determined by the expert in the field with normal trials, or with the usual considerations regarding the formulation.

In all embodiments of the present invention, the effective amount of propanediol mononitrate or chloroform to be administered to the ruminants is preferably selected in the range of 0.05 to 5 propanediol mononitrate or chloroform/animal/day, more preferably in the range of 0.1 to 4 g propanediol mononitrate or chloroform/animal/day, most preferably in the range of 0.5 to 3 g propanediol mononitrate or chloroform/animal/day.

The dosage can vary dependent on the severity of the symptoms, such as once a day up to three times a day.

In all embodiments of the present invention, propanediol mononitrate or chloroform, respectively a composition comprising propanediol mononitrate or chloroform can be administered prophylactically, or when the animal has or is at a particular risk of developing oxidative stress, a reduced immune system and/or faces cartilage problems or pain.

Thus, in a further embodiment, the present invention relates to a propanediol mononitrate or chloroform respectively a composition comprising propanediol mononitrate or chloroform for the use in a method for the treatment or prophylaxis of oxidative stress, inflammation, muscle spasm, inflammation and/or arthritis in a ruminant, said method encompassing the step of administering an amount of 0.1 to 5 g, preferably 0.5 to 5 g, more preferably 1 to 3 g of propanediol mononitrate or chloroform/animal/day to a ruminant.

In all embodiments of the present invention, domestic cattle, sheep and goat are the more preferred species. For the present purposes, most preferred species are domestic cattle. The term includes all races of domestic cattle, and all production kinds of cattle, in particular dairy cows and beef cattle.

A particularly preferred group of ruminants in all embodiments according to the present invention are dairy cows, in particular lactating dairy cows or beef cattle.

Dairy cows may be administered propanediol mononitrate or chloroform respectively the composition comprising propanediol mononitrate or chloroform before lactation, during lactation or after lactation onset. If the composition is administered before lactation, this can be from 90 days prior to lactation onset to 1 day prior to lactation onset, preferably from 45 days prior to lactation onset to 10 days prior to lactation onset. The composition may be administered daily prior to lactation onset.

Propanediol mononitrate or chloroform respectively the composition comprising propanediol mononitrate or chloroform may also be administered pre- or post-calving for a suitable number of days. For example, the composition may be administered to the animal for 40 days to 100 days post calving, or for 45 days to 95 days post calving, or for 50 days to 90 days post calving.

The composition according to the present invention may be formulated in any suitable form, including a powder, a granule, a pellet, a solution, or a suspension.

In one embodiment, the composition can be a dry, free-flowing powder (powderous formulation) suitable for direct inclusion into a commercially-available feed or as a supplement to a total mixed ration or diet. The powderous formulation may be mixed with either solid or liquid feed or with water. In another embodiment, the composition can be formed into pellets.

In all embodiments of the present invention, the composition comprising propanediol mononitrate or chloroform preferably is a powderous formulation comprising propanediol mononitrate or chloroform and a carrier material. Suitable carrier includes any carrier well known in the food and feed industry such as silicone dioxide without being limited thereto.

If the composition is a powderous formulation comprising propanediol mononitrate or chloroform and a carrier material, propanediol mononitrate or chloroform is usually sprayed onto or admixed with the carrier material by standard methods in the art, e.g. by using solvent suitable for the preparation of food or feed products such as e.g. dichloromethane followed by evaporation of the organic solvent.

Alternatively, propanediol mononitrate or chloroform can be diluted in a suitable edible oil before being sprayed onto or admixed with the carrier material. The powderous formulation may in addition contain usual additives used in the preparation of powderous formulations for feed application.

The amount of propanediol mononitrate or chloroform in the composition according to the present invention, in particular in a powderous formulation is preferably selected in the range of 1 to 20 wt.-%, preferably in the range of 2 to 15 wt.-%, most preferably in the range of 4 to 12 wt.-%, based on the total weight of the composition.

Propanediol mononitrate or chloroform respectively the composition comprising propanediol mononitrate or chloroform according to the present invention such as in particular the powderous formulation is preferably administered admixed with the animal's feed, wherein the term feed refers to any compound, preparation, mixture, or composition suitable for, or intended for intake by an animal. Exemplary feed for ruminants such as cows include forage (grass, legumes, silage), hay, grass, grain as well as soy without being limited thereto.

When incorporated directly into the animal's feeds, propanediol mononitrate or chloroform respectively the composition comprising propanediol mononitrate or chloroform according to the present invention may be added in amounts ranging from 0.1 to 100 kg per ton, such as from 0.1 to 20 kg per ton (2000 pounds) of feed. In some embodiments, the composition can be added to animal feedstuffs in amounts from 0.1 kg to 50 kg per ton, from 0.1 to 20 kg per ton, or from 0.5 kg to 10 kg per ton of feed. In certain embodiments, the composition may be added to feeds in amounts ranging from 1 to 5 kg per ton of feed.

When expressed as a percentage of dry matter of feed, propanediol mononitrate or chloroform respectively the composition comprising propanediol mononitrate or chloroform may be added to animal feedstuffs in amounts ranging from 0.01 to 2.5% by weight, such as from 0.0125% to 2% by weight. In one embodiment, the composition can be added to animal feedstuffs in amounts from 0.05 to 1.5% by weight, such as from 0.06% to 1% by weight. In another embodiment, the composition can be added in amounts from 0.1 to 0.7% by weight, such as from 0.125% to 0.5% by weight of feed.

Alternatively, propanediol mononitrate or chloroform respectively the composition comprising propanediol mononitrate or chloroform such as in particular the powderous formulation according to the present invention may be fed directly to the animal as a supplement in amounts of from 0.01 gram to 20 gram per kilogram of live body weight per day, such as from 0.01 gram to 10 gram per kilogram, 0.01 gram to 5 gram, 0.01 gram to 1 gram, 0.015 gram to 1 gram, or 0.02 gram to 0.4 gram per kilogram of live body weight per day.

One of skill in the art can appreciate that the amount of propanediol mononitrate or chloroform respectively the composition comprising propanediol mononitrate or chloroform fed can vary depending upon the amount of propanediol mononitrate or chloroform incorporated in the composition, the animal species, the size of the animal and the type of the feedstuff to which the claimed propanediol mononitrate or chloroform respectively the composition comprising propanediol mononitrate or chloroform is added.

Furthermore, the invention relates a propanediol mononitrate or chloroform respectively a composition comprising propanediol mononitrate or chloroform according to the present invention for improving the overall state of health and resistance to diseases of a ruminant by increasing the endogenous methylsulfonylmethane in the rumen fluid, preferably by at least 100%, preferably by at least 200%, more preferably by at least 300% based on the control (i.e. not supplemented with a propanediol mononitrate or chloroform).

The present invention is further described by the following examples which should not be construed as limiting the scope of the invention.

EXPERIMENTAL PART

Eight fistulated Brahman steers (*Bos indicus*) were randomly allocated to two groups (4 animals per group) and received a forage ad libitum diet (Rhode grass hay (*Chloris gayana*), chemical composition: DM, 917 g/kg fresh matter; in g/kg of DM: OM, 806; CP, 169; NDF, 661; ADF, 359; ADL, 46; ash, 116 and GE 17.38 MJ/kg). The treatments used were chloroform fixed in cyclodextrin (reference) and PDMN (10% purity on silicon dioxide). Animals were adapted to the diet over a 21 d period. After that initial period, experimental animals were placed into individual pens in an animal house for the measurement of intakes (10 d) and were treated with cyclodextrin (2 g/100 kg LW) and molasses (60 mL/d). On the last 2 days animals were placed into open-circuit respiration chambers for collection of rumen samples. Following the initial adaption/control period one group of animals received the chloroform+60 mL of molasses during 21 days (1.6 g choloroform-CD/100 kg LW) and the second group received the PDMN treatment during 21 days (2.5 g PDMN/animal/day). PDMN was provided to the animals mixed with molasses (60 mL/day, molasses were previously diluted in water: 1:4 water:molasses) and mixed with the hay at three different times: 0 h, 3 h and 5 h after the feed was offered. PDMN group was treated with comparative amounts of cyclodextrin as the chloroform group during the experiment. On days 20 and 21 of treatment both groups were placed in open-circuit respiration chambers for rumen fluid collection.

Rumen fluid samples (approx. 60 mL per animal) were collected using a probe with 2 layers of cheesecloth through the cannula of the animal at 3 h post feeding, during confinement in respiration chambers to determine rumen metabolites. The metabolites were quantified using Nuclear Magnetic Resonance spectroscopy in the NMR facilities of the Institute for Molecular Bioscience and of the Queensland NMR Network (QNN) at the University of Queensland in analogy to the method as disclosed by Li et al in Plos One, Vol. 9, issue 6, 2014 (pages 1-15).

TABLE 1

Effects of PDMN on rumen metabolites compared with control period (μmol/L rumen fluid).

| Metabolite | Control | PDMN | SEM[a] | P-value |
|---|---|---|---|---|
| Dimethylsulfone | 20 | 113 | 3.84 | 0.001 |
| Trimethylamine | 334 | 1242 | 137 | 0.016 |

[a]SEM, standard error of the mean

TABLE 2

Effects of chloroform on rumen metabolites compared with control period (μmol/L rumen fluid)

| | Control | Chloroform | SEM[a] | P-value |
|---|---|---|---|---|
| Dimethylsulfone | 21 | 80 | 3.85 | 0.007 |
| Trimethylamine | 564 | 828 | 100 | 0.025 |

[a]SEM, standard error of the mean

As can be retrieved, the treatment with propanediol mononitrate or chloroforms propanedialediol mononitrate and chloroform lead to a statistically significant increase of the methyl donor dimethylsulfone and triethylamine, while propanedialediol mononitrate is particularly effective.

The invention claimed is:

1. A method for the non-therapeutic alleviation or prophylaxis of symptoms of oxidative stress, a reduced immune system or cartilage damage of a ruminant, wherein the method comprises the consecutives steps of:
   (a) assessing if the ruminant is in need of treatment for the non-therapeutic alleviation or prophylaxis of symptoms of oxidative stress, a reduced immune system or cartilage damage; and thereafter
   (b) administering to the ruminant in need of the treatment an effective amount of a compound selected from the group consisting of propandiol mononitrate and chloroform or a composition comprising the compound prior to the ruminant experiencing, while the ruminant is experiencing and/or after the ruminant has experienced the symptoms of oxidative stress, a reduced immune system or cartilage damage.

2. The method according to claim 1, wherein step (b) comprises administering the compound or the composition comprising the compound to the ruminant for an effective period of time to reduce oxidative stress, to improve the immune system, to provide healthy cartilage and/or to alleviate pain accompanying inflammatory diseases.

3. The method according to claim 2, wherein the effective period of time is at least 1 day.

4. The method according to claim 1, wherein step (b) comprises administering to the ruminant an amount of 0.1 to 5 g of the propanediol mononitrate or the chloroform/animal/day.

5. The method according to claim 1, wherein the composition that is administered to the ruminant is a powderous formulation comprising the propanediol mononitrate or the chloroform and a carrier material.

6. The method according to claim 5, wherein the carrier material is silicone dioxide.

7. The method according to claim 1, wherein the ruminant is selected from the group consisting of domestic cattle, sheep and goats.

8. The method according to claim 7, wherein the domestic cattle is selected from the group consisting of dairy cows and beef cattle.

9. The method according to claim 8, wherein step (b) is practiced by administering the compound or the composition to the dairy cow before lactation onset.

10. The method according to claim 8, wherein step (b) is practiced by administering the compound or the composition to the dairy cow for a period from 100 days prior to lactation onset to 1 day prior to lactation onset.

11. The method according to claim 8, wherein step (b) is practiced by administering the compound or the composition to the dairy cow during lactation.

12. The method according to claim 3, wherein the effective period of time is at least 3 days.

13. The method according to claim 2, wherein the effective period of time is from 1 day to 200 days.

14. The method according to claim 1, wherein the compound is 1,3-propanediol mononitrate.

* * * * *